United States Patent [19]

Masuho et al.

[11] Patent Number: 5,043,281

[45] Date of Patent: * Aug. 27, 1991

[54] HUMAN MONOCLONAL ANTIBODIES AGAINST CYTOMEGALOVIRUS AND PROCESS FOR PRODUCING SAME

[75] Inventors: Yasuhiko Masuho; Toru Sugano; Yoh-ichi Matsumoto; Shigeki Fujinaga, all of Tokyo, Japan

[73] Assignee: Teijin Ltd., Osaka, Japan

[ * ] Notice: The portion of the term of this patent subsequent to Aug. 21, 2007 has been disclaimed.

[21] Appl. No.: 590,446

[22] Filed: Sep. 27, 1990

Related U.S. Application Data

[63] Continuation of Ser. No. 92,917, Aug. 6, 1987, abandoned.

[30] Foreign Application Priority Data

Dec. 6, 1985 [JP] Japan .................. 60-273504

[51] Int. Cl.$^5$ .................. C07K 15/28; C12N 15/00; C12N 5/00
[52] U.S. Cl. .................. 435/240.27; 435/7.1; 435/172.2; 435/240.26; 435/70.21; 436/548; 530/387; 935/89; 935/95; 935/96; 935/99; 935/100
[58] Field of Search .................. 435/240.27; 530/387

[56] References Cited

U.S. PATENT DOCUMENTS 4,574,116 3/1986 Kaplan .................. 435/70.21

FOREIGN PATENT DOCUMENTS 0198086 8/1986 European Pat. Off. .
WO8602092 4/1986 PCT Int'l Appl. .
2154609 5/1985 United Kingdom .

OTHER PUBLICATIONS

The Journal of Infectious Diseases, vol. 159, No. 3, Mar. 1989, pp. 436-443.
Symposium on Monoclonal Antibodies for Therapy, Prevention and in vivo Diagnosis of Human Disease, Utrecht, The Netherlands, 1989, Develop. biol. Standard, vol. 71, pp. 127-136.
Biochemical and Biophysical Research Communications, vol. 137, No. 1, May 29, 1986, pp. 273-280.
J. Gen. Virol. (1987), 68, pp. 1457-1461.
Journal of Immunological Methods, 131 (1990), 249-255.
Campbell, A., "Monoclonal Antibody Technology", vol. 13, ed. Burdon & Van Knippenberg, Elsevier, NY, *Laboratory Techniques in Biochemistry and Molecular Biology*, pp. 94-99 (1984).
Schwartz, *Compendium of Immunology*, vol. 1, Van Nostrand Reinhold Co., NY, pp. 96-98 (1980).
Howard et al., Annual Review Immunology, 1:307-333 (1980).
Rasmussen et al, *J. Virology*, 55:274-280 (1985).
Rasmussen, L. E., et al, PNAS 81: 876-880, 1984.
Nowinski, R., et al, Science 210:537-539, 1980.
Emanuel, D., et al. J. Immunol., 133:2202-2204, 1984.

*Primary Examiner*—Robert A. Wax
*Assistant Examiner*—M. D. Woodward
*Attorney, Agent, or Firm*—Sughrue, Mion, Zinn, Macpeak & Seas

[57] ABSTRACT

Human monoclonal antibodies against cytomegalovirus. These antibodies can be advantageously used as a diagnostic, or preventive and remedy for cytomegalovirus infectious diseases.

4 Claims, 2 Drawing Sheets

HUMAN MONOCLONAL ANTIBODIES AGAINST CYTOMEGALOVIRUS AND PROCESS FOR PRODUCING SAME

This is a continuation of U.S. patent application No. 07/092,917 filed Aug. 6, 1987 abandoned.

TECHNICAL FIELD

The present invention relates to human monoclonal antibodies (hereinafter abbreviated to MCA) against cytomegalovirus (hereinafter abbreviated to CMV) and a process for producing the same. The object of this invention is to provide human MCA, specific to CMV, which are useful for the diagnosis, prevention, and therapy of CMV infectious diseases.

BACKGROUND ART

CMV is one of the viruses which belong to the herpesvirus group and is composed of DNA, core protein, capsid, and envelope. Scarcely any diseases are caused in most cases when a human being is infected by this virus; however, it sometimes causes fatal infections such as hepatitis seen with an infected newborn who has low immunity and interstitial pneumania found with a patient who is immunosuppressed because of organ transplantation. Accordingly, effective means of diagnosis, prevention, and therapy of such infections have been greatly needed in medical circles. Condie et al. (see American J. Medicine, March 30, 1984, pp. 134-141) report successful cases where administration of human serum immunoglobulin with a high antibody titer to CMV protected bone marrow transplant recipients from CMV infections and interstitial penumonia arising from the same. Human serum immunoglobulin with a high titer is prepared by collecting and fractionating high-titer blood plasma only, the selection of which is made by checking the antibody titer of the serum of donors beforehand. The antibody titer to CMV of serum immunoglobulin thus prepared is at the most 10 times that of serum immunoglobulin prepared from blood plasma collected randomly and collection of such high-titer serum immunoglobulin as this is very difficult to make in sufficient amounts to ensure a stabilized supply.

The production of high-purity antibody, or MCA, has been made possible since the establishment of the hybridoma method by Milstein and Köhler. Rasmussen et al. (see Proc. Natl. Acad. Sci., U.S.A., 81, pp. 876-880, 1984) provided hybridomas capable of producing MCA specific to CMV by fusing mouse myeloma cells and spleen cells of mice immunized with CMV. Several other research groups have obtained mouse MCA specific to CMV (for instance, Goldstein et al., in Infection and Immunity, 38, pp. 273-281, 1982; Pereira et al., in Infection and Immunity, 36, pp. 92414 932, 1982). Of these MCA, few MCA are seen to have enough active capacity to neutralize viruses; however, MCA provided by Rasmussen et al. has a capacity to neutralize CMV at about 10 μg/ml. This neutralizing capacity is very high when compared with high-titer serum immunoglobulin and is expected to be of use for the prevention or remedy of CMV infections. But, being derived from mice, these MCA are recognized as a foreign substance upon administration to humans, thus causing harmful side effects. Therefore, the development of anti-CMV MCA, arising from humans instead of mice, is hoped for.

Human MCA are generally produced from hybridomas obtained by cell fusion between mouse myeloma cells, human myeloma cells, or cells established from other lymphoid tissues and human lymphocytes. They are also produced from lymphoblast cells obtained by transforming human lymphocytes with Epstein-Barr virus. Many attempts have been made since 1980 to develop human MCA but every method has had its own characteristic problem. MCA produced by a hybridoma obtained by cell fusion of mouse myeloma cells with human lymphocytes is not stable, while the cell fusion between human myeloma cells and human lymphocytes is very low in efficiency. Production of MCA from lymphoblast cells obtained by means of EB virus involves problems of low yield and instability. Moreover, EB virus is capable of causing tumors, thus raising a serious problem of safety. The techniques of establishing MCA-producing cells involves great difficulties as described the above; however, there is another serious barrier, we find lying in the means of obtaining MCA specific to specialantigens. It is a problem generally seen in collecting lymphocytes from fully immunized humans. Generally speaking, lymphocytes of normal persons are in many cases sensitized by CMV but its degree of immunity is very low. Therefore, even when hybridomas or lymphoblast cells are established from lymphocytes of normal persons, it is hardly expected to obtain cells producible of anti-CMV MCA.

With regard to human MCA against CMV, a report is made on a single case of establishing a cell line producing the same (see J. Immunol., 133, pp. 2202-2205). According to this report, a MCA-producing cell line is obtained by transforming lymphocytes of normal persons with EB virus. The report, however, contains only one photograph of fluorescence antibody and it is not made clear whether a cell line which produces MCA with secured stability is established or not. Morever, it also is accompanied by the problem of carcinogenecity arising from EB virus as mentioned before and it is apprehended that it may involve a great risk of life upon its in vivo administration. It is also made apparent that this MCA is incapable of neutralizing CMV even if it binds to CMV.

As explained in the above, the hardest problem encountered in efficiently obtaining desired specific human MCA is the difficulty in sufficiently immunizing human lymphocytes with a specific antigen. In a case where mice are used, even an antigen which is harmful in vivo can be given to them and immunization can also be carried out according to a schedule conveniently suited for the purpose. This is impracticable in the case of human beings, since CMV is a pathogen and so far as no vaccine has yet been developed. Thus, it is not allowed morally to give CMV to human beings intentionally for the purpose of immunization. This is another problem that confronts the production of human MCA stably. Both the hybridoma method and the EB virus method have merits and demerits as described in the above.

DISCLOSURE OF THE INVENTION

As the result of an intensive research conducted with the object of obtaining anti-CMV human MCA, the present inventors have succeeded in obtaining hybridomas producible of anti-CMV human MCA by a method in which human lymphocytes in vitro sensitized to CMV or protein or glycoprotein arising from CMV and mouse myeloma cells (in the presence of mitogen)

are subjected to cell fusion. Hybridomas thus obtained and/or a cell line arising therefrom are then cultured and anti-CMV human MCA are obtained from the culture supernatant.

Human MCA of this invention is an antibody which reacts to CMV and/or CMV-infected cells. Of the anti-CMV human MCA of this invention, desirable ones are of the IgG 1 type, which are further classified into two kinds. One kind of MCA recognizes CMV antigen protein with a molecular weight of about 64,000 or plural CMV antigen proteins having antigen protein with a molecular weight of about 64,000 as the chief element. Another kind of MCA recognizes CMV antigen protein with a molecular weight of about 130,000 and one with a molecular weight of about 55,000. The latter is capable of neutralizing CMV and is produced from hybridoma C41 which is deposited with American Type Culture Collection (ATCC) under deposit number HP 9215 or any other similar hybridomas which recognize antigen protein.

BEST MODE OF CARRYING OUT THE INVENTION

Figure 1:
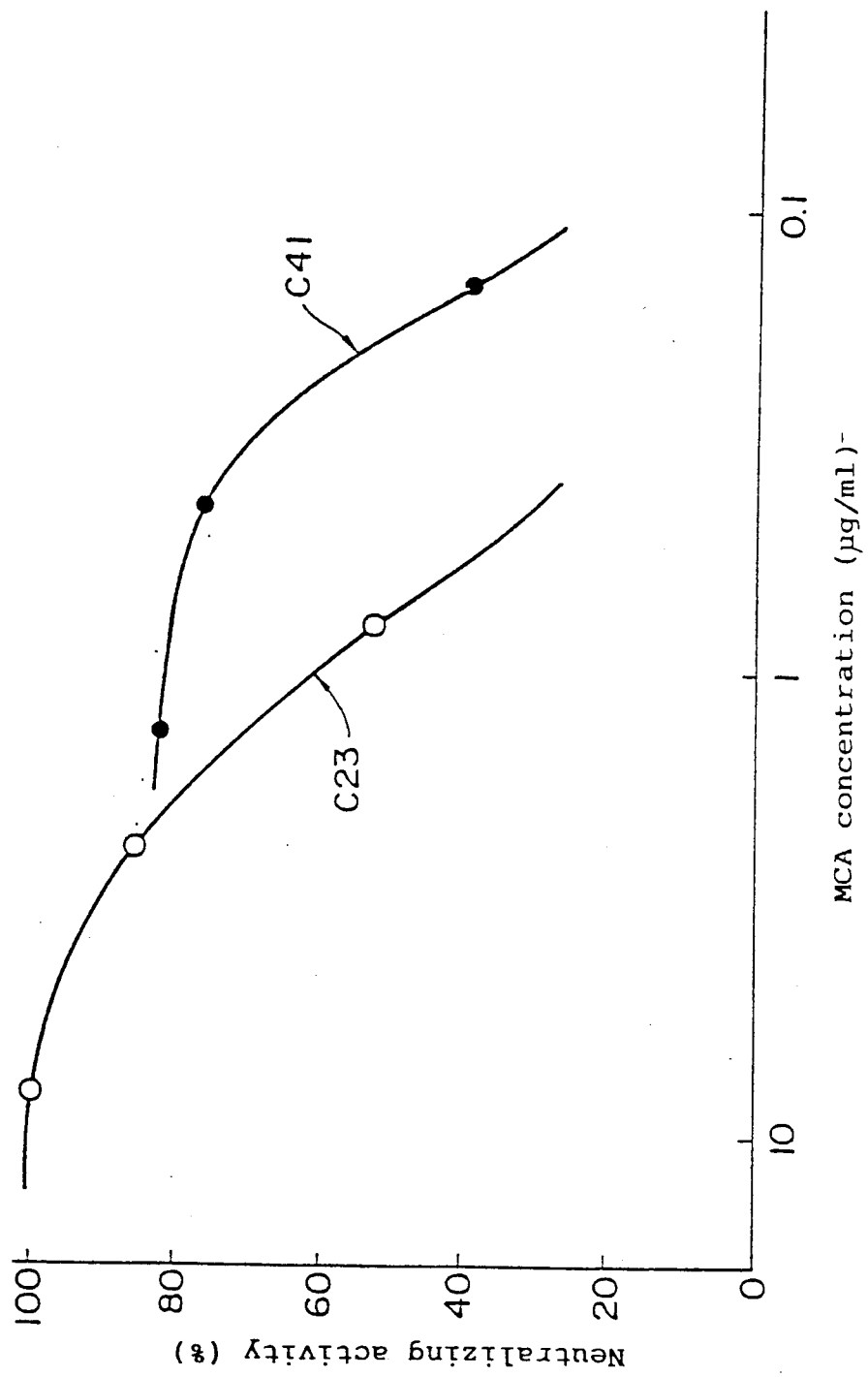
FIG. 1 is a drawing which shows the neutralization activity of anti-CMV human MCA of this invention against CMV.

Human lymphocytes which are used in this invention are found contained in the spleen, lymph node, peripheral blood, bone-marrow, tonsils, and adenoids. Lymphocytes of any source may be used to secure the object of this invention; however, those obtained from the spleen, bone-marrow, and tonsils are preferable.

As the mouse myeloma cells, 8-azaguanine resistant cell lines are advantageously used. There are P3X65Ag8 cell line, P3-NS1/1-Ag4-1 cell line, P3X63AgU1 cell line, SP2/OAg14 cell line, P3X63Ag8.6.5.3 cell line, PMC11-45.6.TG1.7 cell line, and SP-1 cell line of BALB/C mouse among publicly known ones.

In this invention, human lymphocytes are sensitized to antigen in vitro in the presence of mitogen prior to performing cell fusion between the human lymphocytes and mouse myeloma cells. In the case of human beings though there exists lymphocytes producible of antibodies against CMV in normal persons, they are very small in number. There is accordingly very little possibility of obtaining the desired hybridomas. On the contrary, when the method of this invention, in which human lymphocytes are sensitized to an antigen in vitro, is adopted, the lymphocytes, which produce antibody specific to the antigen, start selective differentiation and proliferation and consequently make it possible to obtain the desired MCA-producing hybridomas efficiently.

In the Examples of this invention, AD 169 strain of CMV is used as the sensitizing antigen but other CMV strains for experimental use or clinically separated CMV strains can also be used for sensitization. Instead of CMV itself, its constituent proteins or constituent glycoproteins may also be used.

Any type of mitogen may be used so far as it can promote the differentiation and proliferation of lymphocytes and to give its examples, there are pokeweed mitogen (PWM), B cell growth factor (BCGF), protein A, phytohemagglutinin (PHA), and concanavalin A. Desirable ones are 2–200 $\mu$g/ml PWM and 1/100–$\frac{1}{3}$ volume BCGF.

No limit is specially set to the method and conditions of sensitization; however, advisable conditions include the antigen (CMV, or a protein or a glycoprotein arising from CMV) at a concentration of 1 $\mu$g/ml–1 ng/ml, PWM at a concentration of 2–200 $\mu$g/ml, BCGF at a concentration of 1/100–$\frac{1}{3}$ volume, and lymphocytes (antibody-producing cells) at a concentration of $1 \times 10^5 - 1 \times 10^7$ cells/ml. It is advisable to keep the culture temperature at 35–40° C. and culture time at 4–10 days, preferably 6–8 days. Any liquid culture medium may be used so far as it contains serum of a human being, bovine, equine, etc.; however, a liquid culture medium (such as RPMI 1640) which contains fetal calf serum (FCS) is especially preferable.

The thus obtained antibody-producing human cells sensitized to CMV and mouse myeloma cells are then subjected to cell fusion according to a publicly known method. For instance, lymphocytes and myeloma cells are mixed at a ratio of 10:1–1:100, preferably 1:1–1:10 and a suitable cell fusion solution such as RPMI 1640 which contains about 35% polyethylene glycol (molecular weight about 1,000–6,000) and about 7.5% dimethyl sulfoxide is added to the mixture. After the mixture is stirred at room temperature $-37°$ C. for 1 to several minutes, it is diluted little by little with RPMI 1640 containing 10% ECS. After washing, the mixture is adjusted with HAT (hypoxanthine-aminopterin-thymidine) selective medium to have a cell concentration of $1-5 \times 10^5$ cells/ml. The cells were placed in 0.2 ml portions in a 96-well culture plate to be cultured in 5% $CO_2$ air at 35°–38° C. for 3–4 weeks. In HAT liquid culture medium only hybridomas survive and 8-azaguanine resistant myeloma cells and fused cells between myelomas can not survive (unfused antibody producing cells perish in a course of several days).

After the culture is over, the antibody titer in each liquid culture medium is measured and only such hybridomas that produce antibodies as required are selected and isolated (cloning). The measurement of antibody titer in the liquid culture medium can be made by such a method in which the binding of antibody to antigen is checked such as by radioimmunoassay (RIA), enzyme-linked immunosorbent assay (ELISA), and fluorescent antibody technique and also by a method in which the antibody activity that can hinder the biological activity of virus is measured. Mouse-human hybridoma producible of anti-CMV human MCA of this invention can be freeze-stored. When this hybridoma cell line and/or cell line arising therefrom is mass-cultured by a proper method, the desired human MCA of this invention can be obtained from the culture supernatant. Also, this hybridoma can be transplanted into animals to cause tumor formation and human MCA may be obtained from their abdominal dropsy and serum.

Anti-CMV human MCA thus obtained has the following chracteristic properties. The anti-CMV human MCA obtained by this invention reacts commonly to many kinds of experimental CMV strains and clinically separated strains but does not react to other herpes group including herpes simplex virus, EB virus, and chickenpox herpes zoster virus. It reacts with CMV-infected cells but not with uninfected cells. Therefore, it may be said that these MCA are specific to CMV. Human MCA which have thus been clearly demonstrated to be specific to CMV have for the first time come to be made obtainable by this invention.

CMV are composed of many antigenic substances. As the result of a study made to clarify what CMV constituents the human MCA of this invention react to, it has been made clear that MCA of the first group react to proteins (inclusive of glycoproteins; the same shall apply hereinafter) having a molecular weight of about 64,000 and aggregates of antigen proteins mainly consisting of proteins having a molecular weight of about 64,000. These MCA have no ability to neutralize virus. While MCA of the second group react to proteins having molecular weight of about 130,000 and proteins having molecular weight of about 55,000 and it has been clarified that some of MCA belonging to this group have a strong activity of neutralizing virus. Judging from these properties, MCA belonging to the first group and those belonging to the second group can be used for the diagnosis of CMV infection, while MCA belonging to the second group can be advantageously used for the prevention and therapy of CMV infection.

In this invention, no limit is set forth as to antigenic substances and all human MCA that are specific to CMV are involved in the scope of this invention. It is, however, a very important property for MCA to have an activity of neutralizing (inactivating) virus when judged from the viewpoint of prevention and therapy.

The present invention is described in detail by the following examples.

EXAMPLE 1

(1) Preparation of CMV antigen

HEL cells grown in monolayers were mixed with cells infected by AD 169 strain at a ratio of 7:1 and cultured for 5 days in a $CO_2$ incubator. The infected cells thus obtained were peeled off with phosphate buffer saline containing 0.1% EDTA and collected. The pooled substances were then subjected to ultrasonic breaking for 45 seconds and centrifuged at 3,000 rpm for 20 minutes to obtain supernatant, which was placed on a double-layered sucrose solution, one layer being 66% and the other 20%, and centrifuged at $10,000 \times g$ for 1 hour. Coming together between the 60% layer and the 20% layer by nature, the viruses were collected and dispersed thoroughly by ultrasonic treatment. The dispersion liquid was placed on a $CsCl_2$ solution of $1.28 g/cm^3$ and centrifuged at $100,000 \times g$ for 42 hours. As the result, CMV were found gathering in the $CsCl_2$ solution at a density of $1.29 g/cm^3$ where a density gradient was generated and collected for use as an antigen for in vitro sensitization.

Also, antigen for ELISA use were prepared as follows. HEL cells infected with AD 169 were cultured in a $CO_2$ incubator and infected cells were collected when all the cells were observed having developed cell denaturation. These cells were ultrasonically treated for 3 minutes and centrifuged at 3,000 rpm for 20 minutes to obtain the supernatant. This was used as an antigen for ELISA use.

(2) Sensitization of lymphocytes with CMV

Human spleen lymphocytes were suspended in a liquid culture medium A (RPMI 1640+20% fetal calf serum+20mM HEPES+2mM glutamine+1mM Na pyruvic acid +0.02mg/ml serine+80 µg/ml gentamicin), whose cell density was $12 \times 10^5$ s cells/ml. This cell suspension was placed in 15 wells of a 24-well culture plate in portions of 1 ml. They were divided into 5 groups of 3 wells, and the first group had nothing added thereto, the second group had CMV antigen 12 ng protein/ml added thereto, the third group had 10 ml of BCGF, the fourth group had the same amount of CMV and BCGF, and the fifth group had CMV and 20 µg/ml of PWM. The culture plate was incubated at 37° C. in 5% $CO_2$ air for 6 days.

(3) Cell fusion with mouse myeloma cells, $P3 \times 63Ag$ 8U1 cell line (abbreviated to P3U1)

P3U1 had been cultured beforehand in a liquid culture medium B (RPMI 1640+10% fetal calf serum+2mM glutamine+80 µg/ml gentamicin). The cell density at the time of its use was $6 \times 10^5$ cells/ml. Five groups (of 3 wells) of sensitized lymphocytes obtained in the preceding (2) and P3U1 were separately washed twice with serum-free RPMI 1640. Lymphocytes in the 3 wells of the respective groups and $5 \times 10^6$ cells of P3U1 were placed together in test tubes. They were centrifuged at 1,500 rpm for 5 minutes and the supernatants were discarded. Cell pellets were dispersed thoroughly by tapping the test tubes. 0.5 ml of polyethylene glycol solution (RPMI 1640 5.75 ml+polyethylene glycol 100 3.5 ml+dimethyl sulfoxide 0.75 ml) (hereinafter referred to as "PEG solution") was added to each test tube allowing cells to suspend in the solution gently. One minute later 0.5 ml of RPMI 1640, another 1 minute later 1 ml of RPMI 1640, another 2 minutes later 4 ml of HAT liquid culture medium (RPMI 1640+20% fetal calf serum+80 µg/ml of gentamicin+95 µM hypoxanthine+0.4 µM aminopterin+1.6 µM thymidine), and another 2 minutes later 4 ml of HAT liquid culture medium were added, thus finally making up a total of 25 ml of cell suspending solution. This solution was seeded in a culture plate (96 wells) and cultured at 37° C. in 5% $CO_2$ air. Half of the medium was exchanged for a fresh HT culture medium (omitting A from HAT medium) every week repeatedly, thus obtaining hybridoma.

(4) Measurement of human IgG and CMV antibody

The measurement was made by ELISA. For making the measurement of human IgG, goat antihuman IgG antibody (10 µg/ml), and for making the measurement of anti-CMV antibody, 2 µg protein/ml of CMV (AD 169 strain) were respectively coated to Falcon microtest III 96-well plates in portions of 50 µl/well. 60 µl of hybridoma culture supernatant was added to the plates and left standing at room temperature for 1 hour. After having been washed three times with Hank's balanced salt solution buffer (HBSS-B) containing 1% bovine serum albumin (BSA), the plates had 60 µl of anti-goat human IgG antibody-alkaline phosphatase (2000-fold diluted solution) added and were made to go through reaction at room temperature for 1 hour. The plates were again washed 3 times with HBSS-B and then 100 µl of a solution prepared by dissolving p-nitrophenylphosphate in 1M diethanolamine+1 mM $MgCl_2$ solution of pH 9.5 at a ratio of 0.6 mg/ml was added thereto. About 30 to 60 minutes thereafter, the absorbance at 405 nm was measured and the required values were calculated by comparing the measurement with that of standard IgG solution or standard CMV positive serum.

All the groups had their cells seeded to the respective 96-well plates and the number of wells in which hybridomas were generated (observed by the naked eye), furthermore, the number of wells in which said hybridomas had produced human IgG, and the number of wells in which anti-CMV antibodies had been produced were counted and shown in Table 1. When CMV and BCGF were added, the largest number of anti-CMV antibody-producing hybridomas were generated.

TABLE 1

| | in vitro sensitization | Number of wells having hybridomas (observed by naked eye) | IgG producing | Anti-CMV producing |
|---|---|---|---|---|
| 1 | Nothing added | 18 | 12 | 0 |
| 2 | CMV | 20 | 27 | 1 |
| 3 | BCGF | 81 | 93 | 6 |
| 4 | CMV + BCGF | 84 | 96 | 32 |
| 5 | CMV + PWM | 55 | 29 | 3 |

EXAMPLE 2

Human spleen lymphocytes were sensitized with CMV or PWM according to Example 1, (2), and cell-fused with P3U1 according to Example 1, (3). Of the hybridomas thus obtained, those hybridomas which had produced MCA were subjected to cloning as follows.

(1) Cloning of hybridomas

Cloning was performed by limiting dilution. Cells were taken out of anti-CMV antibody positive wells and were seeded in portions of 1 cell/well or 10 cells/-well in the respective well containing a liquid culture medium B. Cells were found grown proliferously enough 2 weeks later, and it was checked by ELISA if there were anti-CMV.MCA in the supernatants, thus selecting hybridomas which were producible of anti-CMV.MCA.

In this way, hybridomas C1, C3, C4, C7, C23 and C41 were established. These hybridomas are since continuing stably to produce anti-CMV.human MCA of IgG type. Hybridoma C41 was diposited with American Type Culture Collection (ATCC) on Sept. 29, 1986, under deposit number HB 9215.

(2) Preparation of anti-CMV.human MCA

C41, one of the hybridomas obtained in the above, was cultured in a serum-free ITES culture medium (RPMI 1640 2 volumes+Dulbecco's MEM 1 volume+F12 1 volume+insulin 8.5 $\mu$g/ml+transferrin 2 $\mu$g/ml+ethanolamine 2 $\mu$M+selenite $2.5\times10^{-8}$M). Its culture supernatant was concentrated by ultrafiltration (Amicon P30) and dialyzed against 0.02 M sodium phosphate (pH 7.8). The dialyzate was put to DE 52 column (PHarmacia) equilibrated with the same buffer and recovered human MCA from unadsorbed fractions. Upon analysis by sodium dodecyl sulfate-polyacrylamide gel electrophoresis (SDS-PAGE), it was confirmed to be a varified MCA preparation comprising H-chain and L-chain.

EXAMPLE 3

(1) Reactivity of anti-CMV.human MCA to infected cells

Anti-CMV.human MCA C1, C3, C4, C7, C23 and C41 were made to react to HEL cells infected with AD 169 strain of CMV or Hi-1 strain and to those not infected cells. Further, fluorescein isothiocyanate (FITC)-labeled human IgG antibodies were made to react to them and were observed under a fluorescence microscope. The result showed that all MCA did not react to the uninfected cells but reacted only to infected cells. It was also found that C1, C3, C4, and C7 reacted to CMV antigen in the cytoplasm of cells infected with AD 169 or Hi-1 but did not react to CMV antigen on their cell membrane. On the other hand, C23 and C41 reacted to both CMV antigen in the cytoplasm and CMV antigen on the cell membrane.

(2) Reactivity of anti-CMV.human MCA to solubilized virus antigen

With the object of studying the binding activity of anti-CMV.MCA to herpesviruses, solubilized antigens were prepared according to Example 1, (1), from HEL cells infected respectively with 2 strains of HSV-1, 2 strains of HSV-2, 2 strains of VZV, 6 strains of CMV, and 1 strain of EBV and unifected HEL cells, and ELISA was performed with them according to Example 1, (4). The result is shown in Table 2.

Anti-CMV.MCA (C1, C2, C3, C7, C23, and C41) were all found to bind to CMV only but not to bind to other herpesvirus and host cells. Anti-CMV.MCA, except for C41, were found to bind to all the 6 strains of CMV. Incidentally, H1 is human MCA against herpes simplex virus (HSV).

TABLE 2

| | Human MCA | | | | | | |
|---|---|---|---|---|---|---|---|
| Virus strain | C1 | C3 | C4 | C7 | C23 | C41 | H1 |
| CMV | *1 | | | | | | |
| AD169 | 1.60 | 1.32 | 1.50 | 1.47 | 0.17 | 0.49 | — |
| Hi-1 | 0.78 | 0.21 | 0.29 | 0.22 | 0.28 | 0.46 | — |
| Onoda | 0.88 | 0.34 | 0.53 | 0.38 | 0.46 | 0.82 | — |
| No. 12 | 1.00 | 0.23 | 0.24 | 0.22 | 0.52 | — | — |
| Omine | 0.95 | 0.40 | 0.62 | 0.60 | 0.98 | 1.25 | — |
| YAN-3 | 1.20 | 0.34 | 0.40 | 0.46 | 0.19 | — | — |
| HSV-1 | *2 | | | | | | |
| KOS | — | — | — | — | — | — | 1.61 |
| Fujinaga | — | — | — | — | — | — | 2.00 |
| HSV-2 | | | | | | | |
| UW268 | — | — | — | — | — | — | 1.73 |
| YS4 | — | — | — | — | — | — | 1.67 |
| VZV | | | | | | | |
| Oka | — | — | — | — | — | — | — |
| Batson | — | — | — | — | — | — | — |
| EBV | | | | | | | |
| B95-8 | — | — | — | — | — | — | — |
| Not infected | | | | | | | |
| HEL | — | — | — | — | — | — | — |

*1 The values indicate absorbance at 405 nm.
*2 Less than 0.1.

EXAMPLE 4

Virus neutralizing activity of anti-CMV. human MCA

A mixture of 200 $\mu$l of human MCA solution, 100 $\mu$l of 5-fold diluted solution of 200 CH50/ml of fresh guinea pig serum, and 100 $\mu$l of solution containing 737 pfu (plaque-forming units) of CMV (AD 169 strain) was incubated at 37° C. for 1 hour. After 100 $\mu$l of this mixed solution was spread over HEL cells incubated in a 6-well plate and again incubated at 37° C. for 1 hour, MEM medium which contained 0.5% (W/V) agarose and 5% (V/V) FCS was added thereto and incubated for 11 days in a CO$_2$ incubator. The resulting single-layer cells were fixed with a 10% formalin solution and stained with a 0.3% Methylene Blue solution to determine the plaque-forming units (pfu) of CMV-infected cells. The neutralizing activity was calculated as follows.

$$\frac{\begin{pmatrix} pfu \text{ of sample with} \\ \text{no } MCA \text{ added} \end{pmatrix} - \begin{pmatrix} pfu \text{ of sample with} \\ MCA \text{ added} \end{pmatrix}}{(pfu \text{ of sample with no } MCA \text{ added})} \times 100(\%)$$

The result is shown in FIG. 1. 50% neutralization was indicated by C23 at 0.75 μg/ml and by C41 at 0.18 μg/ml; however, C1, C3, C4, and C7 showed no neutralization activity. In case where Hi-1 strain was used, C23 showed 10% neutralization at 3.3 μg/ml and C41 showed 100% neutralization at 0.95 μg/ml, while C3 showed only 35% neutralization at 17.7 μg/ml.

Upon determination of neutralizing activity of 5 strains of CMV strains excepting AD 169 strain, C23 showed 95% or more of neutralization for all virus strains at 10 μg/ml. While C41 showed, corresponding closely to the ELISA data given in Table 2 of Example 3, (2), somewhat low neutralizing activity of 20% and 64% to No.12 strain and YAN-3 strain respectively and more than 80% neutralizing activity to other strains.

EXAMPLE 5

Immunoprecipitation analysis of anti-CMV. human MCA

Immunoprecipitation analysis was conducted to determine what viral constituent(s) those human MCA react with. HEL cells wer infected with CMV (AD 169 strain) and isotope-labeled with 35S-methionine. The labeled cells were dissolved in a solution comprising 0.01M Tris. HCl+0.15 M NaCl+1% sodium deoxycholate+1% Triton X 100+0.1% sodium dodecyl sulfate (SDS)+1 mM phnyl methyl sulfonyl fluoride (pH 7.4). Anti-CMV.human MCA was added thereto to generate an antigen-antibody complex which was then subjected to adsorption purification by use of protein A - Sepharose 4B. The purified product was heat-treated at 100° C. for 3 minutes in a solution of 0.125 M Tris.HCl+1% SDS+3% 2-mercaptoethanol+15% glycerin (pH 8.2) and the resulting supernatant was subjected to SDS-polyacrylamide gel electrophoresis. After the electrophoresis was over, the gel was dried and exposed to X-ray film at −70° C.

Figure 2:
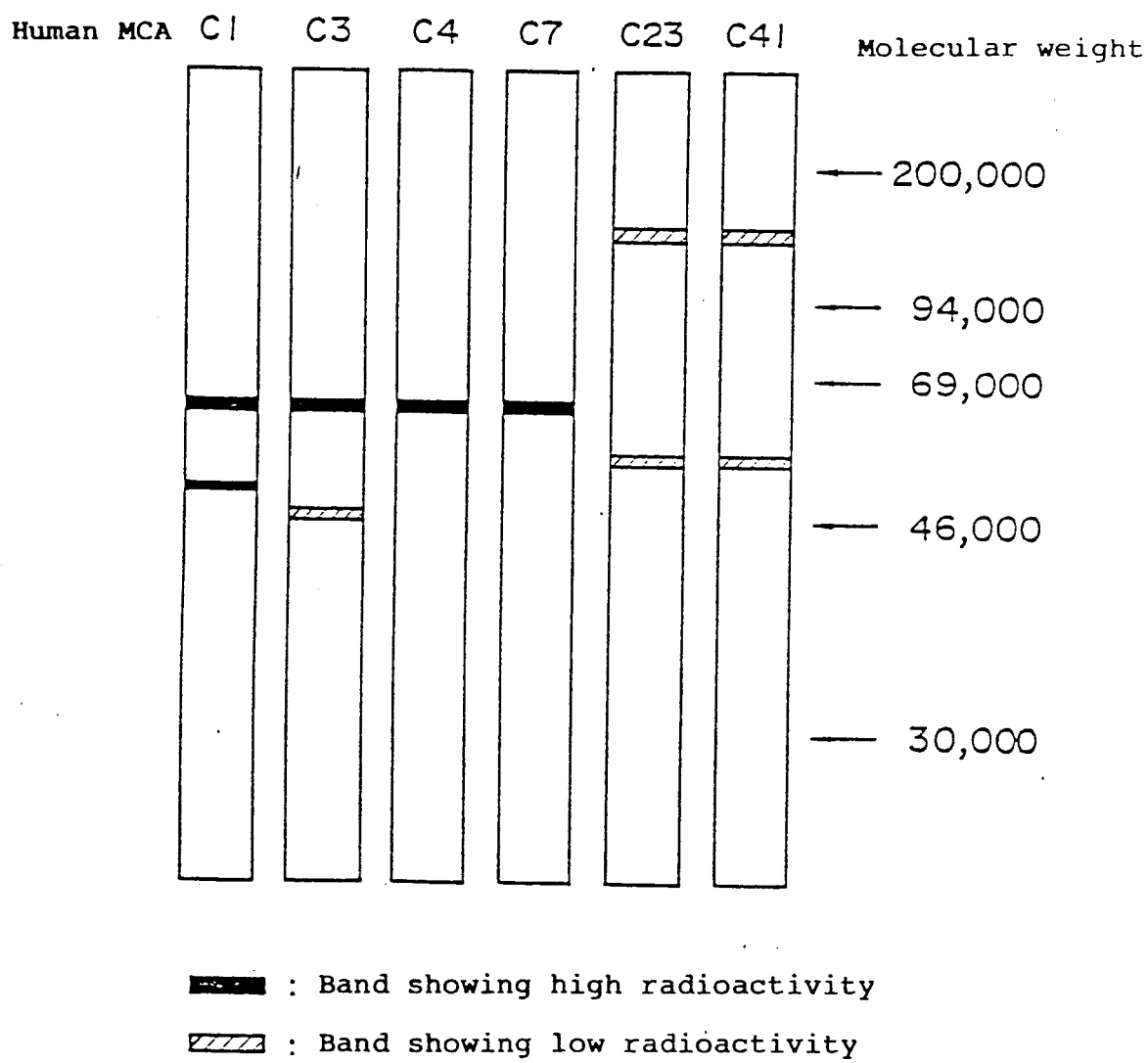
FIG. 2 is a drawing to show the result of immunoprecipitation assay of anti-CMV human MCA of this invention.

The result is shown in FIG. 2. It has been found that C1 reacts with virus antigens having molecular weights of about 64,000 and about 50,000, C2 reacts with the ones having molecular weights of about 64,000 and about 46,000 C4 and C7 react with the one having a molecular weight of about 64,000, and C23 and C41 react with the ones having molecular weights of about 130,000 and about 55,000.

EXAMPLE 6

Isotypical identification of anti-CMV.human MCA

Isotypical identification of human MCA was carried out as follows. Identification of H-chain was made by the immunodiffusion test (Ouchterlony test) with the use of rabbit antiserum against human IgG1, IgG2, IgG3, and IgG 4. Identification of L-chain was conducted by ELISA in which AD169-infected cells were used as antigen plate and alkaline phosphatase-labeled goat anti-human K-chain or λ-chain was used as secondary antibody.

The result is shown in Table 3.

TABLE 3

| MCA | C1 | C2 | C3 | C4 | C23 | C41 |
|---|---|---|---|---|---|---|
| Isotype | IgG1,λ | IgG1,λ | IgG1,λ | IgG1,λ | IgG1,λ | IgG1,λ |

INDUSTRIAL APPLICATIONS

Anti-CMV.human MCA of the present invention can be advantageously used as a diagnostic for CMV infections and also as a preventive and a remedy for CMV infectious diseases.

We claim:

1. Human monoclonal antibodies against cytomegalovirus that
   1) recognize cytomegalovirus antigen proteins having molecular weights of about 130,000 and about 55,000, and
   2) are capable of neutralizing cytomegalovirus.

2. Human monoclonal antibodies against cytomegalovirus that
   recognize cytomegalovirus antigen proteins having molecular weights of about 55,000 and about 130,000 and
   are produced by hybridoma C41 which is deposited with the American Type Culture Collection (ATCC) under deposit number HB9215.

3. A process for producing human monoclonal antibodies against cytomegalovirus comprising the steps of:
   (1) sensitizing human lymphocytes;
   (2) fusing said sensitized human lymphocytes from step (1) with mouse myeloma cells;
   (3) selecting hydridomas resulting from step (2) that produce antibodies against cytomegalovirus;
   (4) culturing said selected hybridomas from step (3) or a cell line arising therefrom; and
   (5) obtaining human monoclonal antibodies from said cultured hybridomas or cell line of step (4); wherein them improvement comprises
   sensitizing said human lymphocytes in vitro, in the presence of B cell growth factor (BCGF), to
      (a) cytomegalovirus or
      (b) proteins or glycoproteins arising from cytomegalovirus.

4. Hybridoma C41 which is deposited with ATCC under deposit number HB9215.

* * * * *